US00PP23705P2

(12) United States Plant Patent
Kitahara

(10) Patent No.: US PP23,705 P2
(45) Date of Patent: Jul. 2, 2013

(54) ***PHLOX* PLANT NAMED 'PPPHL07201'**

(50) Latin Name: *Phlox subulata×stolonifera*
Varietal Denomination: PPPHL07201

(75) Inventor: Akiko Kitahara, Mizuho (JP)

(73) Assignee: Amerinova Properties, Bonsall, CA (US)

( * ) Notice: Subject to any disclaimer, the term of this patent is extended or adjusted under 35 U.S.C. 154(b) by 86 days.

(21) Appl. No.: 13/317,207

(22) Filed: Oct. 12, 2011

(51) Int. Cl.
*A01H 5/00* (2006.01)

(52) U.S. Cl.
USPC ..... Plt./320

(58) Field of Classification Search
USPC ..... Plt./320
See application file for complete search history.

*Primary Examiner* — Susan McCormick Ewoldt
(74) *Attorney, Agent, or Firm* — Cassandra Bright

(57) ABSTRACT

A new and distinct *Phlox* cultivar named 'PPPHL07201' is disclosed, characterized by vigorous plant growth and early flowering, with blooms produced over a long period of time. Plants have a good resistance to powdery mildew and produce violet-blue flowers with a dark eye. The new variety is a *Phlox*, normally produced as an outdoor ornamental plant for containers or gardens.

2 Drawing Sheets

Figure 1:
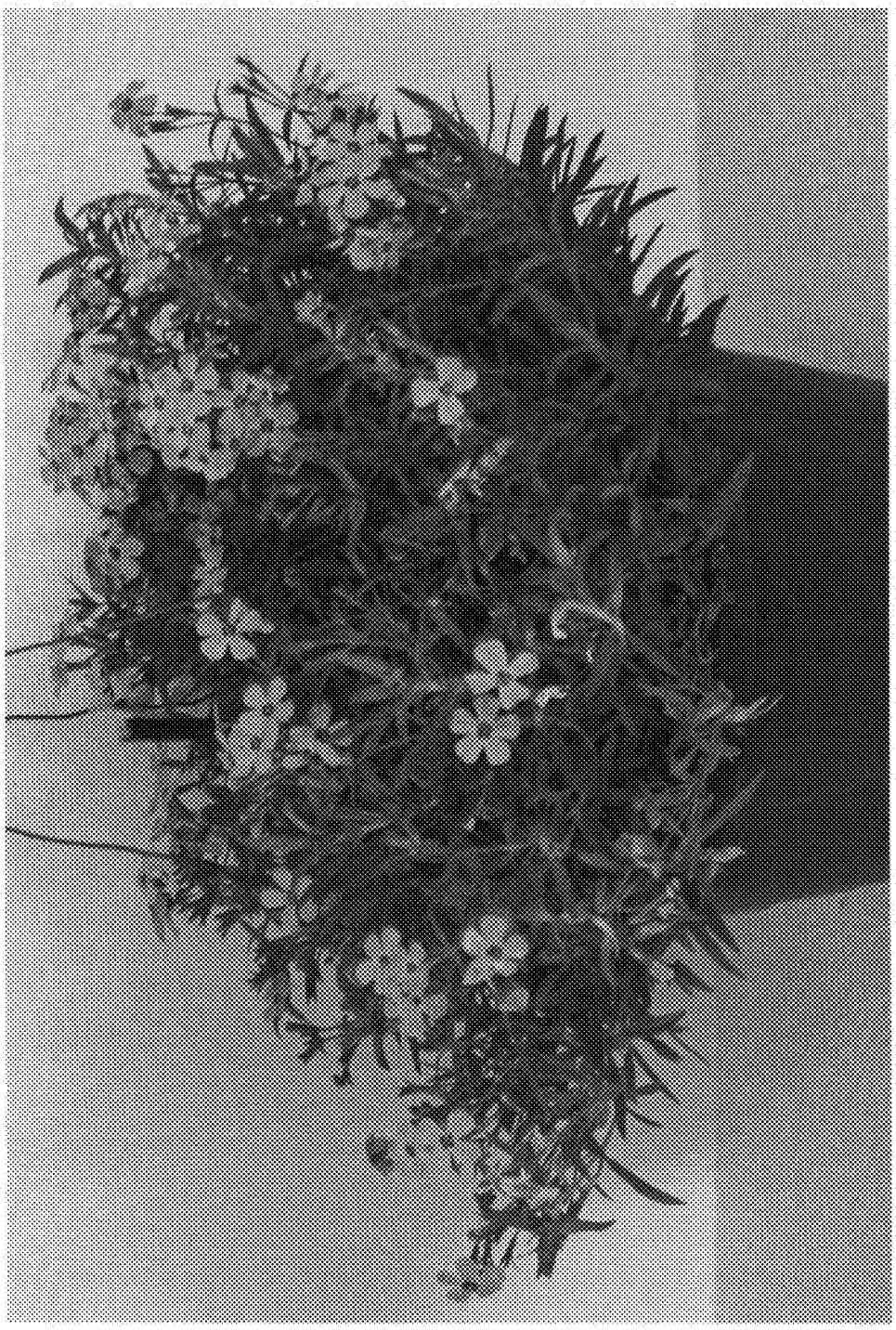

Latin name of the genus and species: *Phlox subulata× stoloniftra.*

Variety denomination: 'PPPHL07201'.

BACKGROUND OF THE INVENTION

The new cultivar was discovered as a result of a planned breeding program directed by the inventor, Akiko Kitahara, a citizen of Japan. The seed parent is an unnamed, unpatented variety of *Phlox subulata* and the pollen parent is an unnamed, unpatented variety of *Phlox stolonifera*. The cross resulting in 'PPPHL07201' was made Apr. 20, 2006. The new variety was discovered Sep. 20, 2007, by the inventor in a non-commercial nursery in Higashiomi Shiga, Japan.

Asexual reproduction of the new cultivar 'PPPHL07201' by vegetative cuttings was first performed Sep. 25, 2007 at a non-commercial nursery in Higashiomi Shiga, Japan. Multiple generations have since been produced and have shown that the unique features of this cultivar are stable and reproduced true to type in successive generations. The new cultivar was first sold and made available to the public in April 2011.

SUMMARY OF THE INVENTION

The cultivar 'PPPHL07201' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'PPPHL07201' These characteristics in combination distinguish 'PPPHL07201' as a new and distinct *Phlox* cultivar:

1. Vigorous growth habit, compared to existing *Phlox subulata* varieties.
2. Early flowering.
3. Long flowering period.

4. Good resistance to powdery mildew.
5. Light violet-blue flowers with a dark eye.

PARENT COMPARISON

Plants of the new cultivar 'PPPHL07201' are similar to plants of the seed parent, *Phlox subulata*, unnamed, in most horticultural characteristics, however, plants of the new cultivar 'PPPHL07201' produce flowers over a significantly longer period than the seed parent. Flower color of the new variety is violet-blue, whereas the seed parent produces purple-pink flowers. Additionally, plants of the new variety are much more vigorous and produce larger flowers than the seed parent.

Plants of the new cultivar 'PPPHL07201' are similar to plants of the pollen parent *Phlox stolonifera* in most horticultural characteristics, however, plants of the new cultivar 'PPPHL07201' produce flowers over a significantly longer period than the pollen parent. Flower color of the new variety is violet-blue, with a dark eye, whereas the pollen parent produces light blue flowers. Additionally, the new variety has smaller foliage than the pollen parent.

COMMERCIAL COMPARISON

'PPPHL07201' can be compared to the commercial variety *Phlox subulata* 'Oakington Blue Eyes', unpatented. The two varieties are very similar in most horticultural characteristics, however, plants of 'PPPHL07201' are more vigorous and produce flowers with a dark eye not found on flowers of 'Oakington Blue Eyes'. Additionally, plants of 'PPPHL07201' are more mounding in growth habit compared to the flat, mat forming habit of 'Oakington Blue Eyes'. Plants of 'PPPHL07201' produce flowers from Spring through Summer, whereas 'Oakington Blue Eyes' produces flowers only during Spring.

'PPPHL07201' can be compared to the commercial variety *Phlox subulata* 'Emerald Blue', unpatented. The two varieties are very similar in most horticultural characteristics, however, plants of 'PPPHL07201' are more vigorous than 'Emerald Blue' and produce flowers with a dark eye not found on flowers of 'Emerald Blue'. Additionally, plants of 'PPPHL07201' are more mounding growth habit compared to the flat, mat forming habit of 'Emerald Blue'. Plants of 'PPPHL07201' produce flowers over a longer period of time, from Spring through Summer, compared to the Spring only bloom of 'Emerald Blue'.

BRIEF DESCRIPTION OF THE PHOTOGRAPHS

The accompanying photograph in FIG. 1 illustrates in full color a of typical plant of 'PPPHL07201' grown in a poly house, in Bonsall, Calif., in a commercial 10 inch container.

Figure 2:
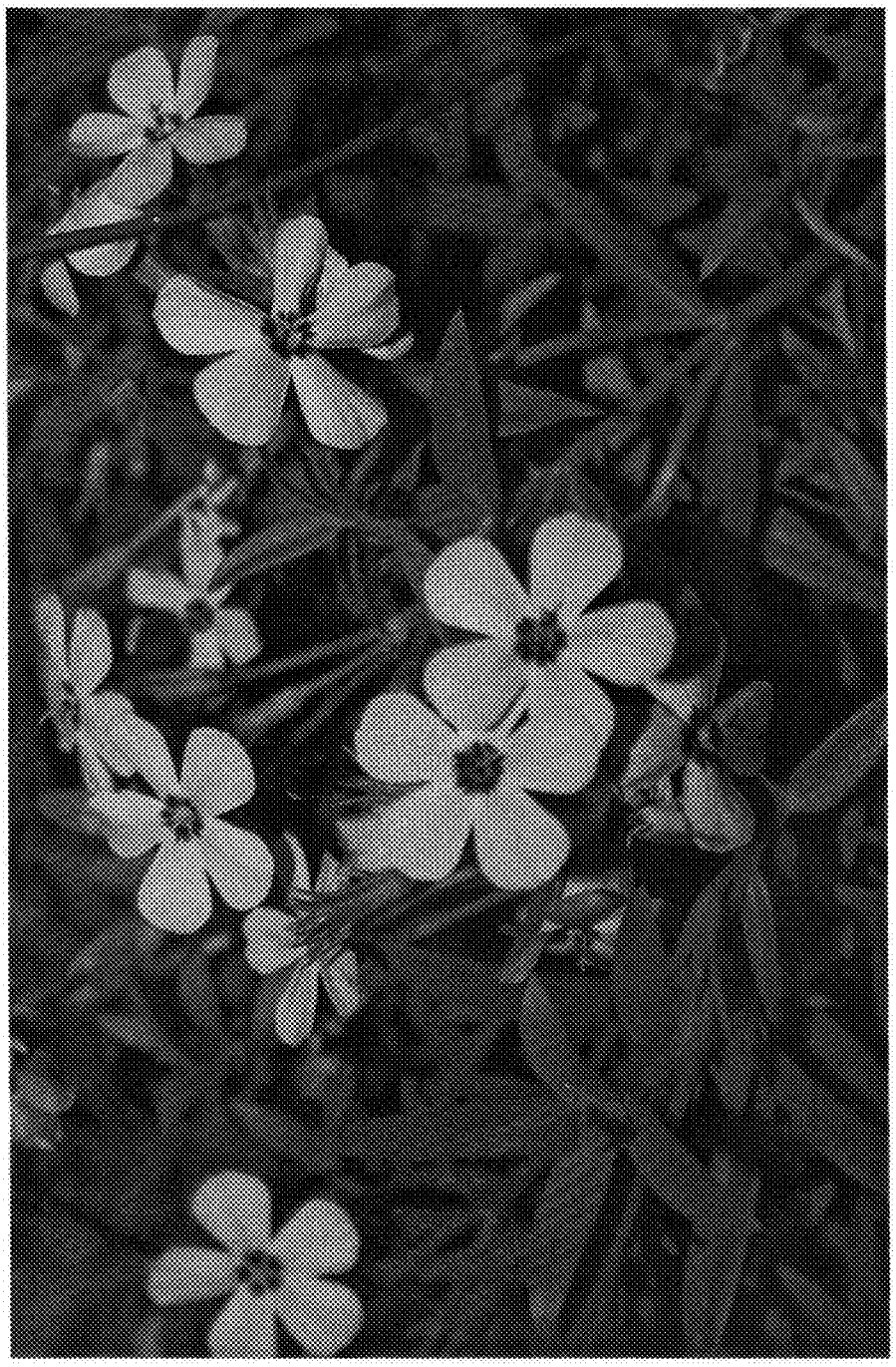

FIG. 2 illustrates in full color a close up view of flowers of 'PPPHL07201'. Age of the plant photographed is approximately 28 weeks from a rooted cutting. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2001 except where general terms of ordinary dictionary significance are used. The following observations and measurements describe 'PPPHL07201' plants grown in a poly house, in Bonsall, Calif., in a commercial 10 inch container. The growing temperature ranged from 60° F. to 75° F. daytime and 50° F. to 60° F. at night. No chemical treatments were given. Measurements and numerical values represent averages of typical plant types.

Botanical classification: *Phlox subulata×stolonifera* 'PPPHL07201'.

PROPAGATION

Time to initiate roots during summer: Approximately 6 days at temperatures between 17° C. and 29° C.

Time to initiate roots during winter: Approximately 5 days at temperatures between 17° C. and 21° C.

Time to produce a rooted cutting: 30 to 35 days.

Root description: Fine, fibrous, moderately dense rooting habit.

PLANT

Pot size of plant described: 25 cm diameter basket.

Age of plant described: Approximately 25 Weeks.

Growth habit: Mounding, spreading.

Height:

- *To top of flowers*.—Approximately 20 cm.
- *To top of foliage plane*.—Approximately 19 cm.

Plant spread: Approximately 45 cm.

Growth rate: Rapid.

Branching characteristics: Very well branched.

Length of primary lateral branches: Approximately 12 cm.

Quantity of primary lateral branches: More than 50 per plant.

Characteristics of primary lateral branches:

- *Form*.—Round.
- *Diameter*.—Approximately 0.2 cm.
- *Color*.—Near RHS Green 143C.
- *Texture*.—Densely pubescent. Hairs minute, less than 0.1 cm.
- *Strength*.—Flexible, moderately strong.

Internode length: Average between 1.5 cm to 2.5 cm.

FOLIAGE

Leaf:

- *Arrangement*.—Opposite.
- *Quantity*.—Approximately 10 per branch.
- *Average length*.—Approximately 3.7 cm.
- *Average width*.—Approximately 0.7 cm.
- *Shape of blade*.—Linear.
- *Apex*.—Acute.
- *Base*.—Blunt.
- *Margin*.—Entire.
- *Texture of top surface*.—Pubescent.
- *Texture of bottom surface*.—Pubescent.
- *Aspect*.—Very slightly recurved to flat.
- *Color*.—Young foliage upper side: Near RHS Green 137B. Young foliage under side: Near RHS Green 137C. Mature foliage upper side: Near RHS Green 137A, but darker. Mature foliage under side: Near RHS Green 137B.
- *Venation*.—Type: Pinnate. Venation color upper side: Indistinguishable from foliage coloration. Venation color under side: Indistinguishable from foliage coloration.
- *Petiole*.—Sessile, petiole not present.

FLOWER

Natural flowering season: Spring through Summer.

Inflorescence and flower type and habit: Clustered cymes of salverform flowers. 2 to 5 cymes, of 3 to 5 flowers.

Rate of flower opening: 3 to 5 days from bud to fully opened flower.

Flower longevity on plant: Approximately 7 to 10 days.

Approximate quantity of flowers per plant: Approximately 70 to 90.

Persistent or self-cleaning: Persistent.

Inflorescence:

- *Depth*.—Approximately 7 cm.
- *Width*.—Approximately 10 cm.

Individual cyme:

- *Depth*.—Approximately 3.5 cm.
- *Width*.—Approximately 4.5 cm.

Bud:

- *Shape*.—Cylindric.
- *Length*.—Approximately 1.5 cm
- *Diameter*.—Approximately 0.3 cm
- *Color*.—Near RHS Violet-Blue 91A.

Flower size:

- *Length*.—Approximately 1.7 cm.
- *Diameter*.—Approximately 1.7 cm.
- *Flower tube length*.—Approximately 1.7 cm
- *Flower tube diameter at basal end*.—Approximately 0.3 cm.
- *Flower tube diameter at distal end*.—Approximately 0.5 cm.

Petals:

- *Length from throat*.—Approximately 1.0 cm.
- *Width*.—Approximately 0.7 cm.
- *Quantity*.—5.
- *Texture*.—Glabrous.
- *Apex*.—Obtuse.
- *Margin*.—Entire.

Color:

*When opening*.—Upper surface: Near RHS Violet-Blue 91A. Lower surface: Near RHS Violet-Blue 91B.

*Fully opened*.—Upper surface: Near RHS Violet-Blue 91B. Flush at base near Violet-Blue 95A. Lower surface: Near RHS Violet-Blue 92C. Flower throat (inside): Near RHS Violet-Blue 92D. Flower throat, visible rim: Near RHS Violet-Blue 95A. Flower tube (outside): Near RHS Violet-Blue 92C, lower section 92D.

*Fading*.—Petals fading to: Near RHS Violet-Blue 90C, with streaks near Purple-Violet N81B.

Calyx/sepals:

*Quantity per flower*.—5.

*Shape*.—50% fused together, linear shape.

*Length*.—Approximately 1.0 cm.

*Width*.—Approximately 0.2 cm.

*Apex*.—Acute.

*Base*.—Fused.

*Margin*.—Entire.

*Texture*.—Pubescent.

*Color*.—Upper Surface: Near RHS Green 137A near apex, base near 143C. Lower Surface: Near RHS Green 137A near apex, base near 143C.

Peduncle:

*Length*.—Average 2.2 cm.

*Diameter*.—Average 0.2 cm.

*Color*.—Near RHS Green 143C.

*Texture*.—Pubescent.

*Orientation*.—Approximately 25° angle from stem, undulating.

Pedicel:

*Length*.—Approximately 1.0 cm.

*Diameter*.—Approximately 0.1 cm.

*Color*.—Near RHS Green 143C.

*Texture*.—Pubescent.

*Orientation*.—Approximately 15° angle from peduncle, undulating.

Fragrance: Musty.

REPRODUCTIVE ORGANS

Stamens:

*Number*.—5.

*Filament length*.—Fused to petals, unfused portion 0.1 cm.

Anthers:

*Length*.—0.1 cm.

*Shape*.—Linear.

*Color*.—Near RHS Yellow 13A.

*Pollen*.—Color: Near Yellow 13A. Quantity: Scant.

Pistil:

*Number*.—1.

*Length*.—1.5 cm.

*Style*.—Length: 1.4 cm. Color: Near RHS Yellow-Green 145D.

*Stigma*.—Shape: forked. Color: Near RHS Yellow-Green 154D. Ovary Color: Near RHS Green 143C.

OTHER CHARACTERISTICS

Seeds and fruits: Not observed to date.

Disease/pest resistance: Resistance to powdery mildew has been observed.

Temperature tolerance: Tolerant to least −1° C. without damage. Upper temperature tolerance to at least 30° C.

What is claimed is:

1. A new and distinct cultivar of *Phlox* plant named 'PPPHL07201' as herein illustrated and described.

* * * * *